United States Patent [19]

Takahashi et al.

[11] Patent Number: 4,760,153

[45] Date of Patent: Jul. 26, 1988

[54] PROCESS FOR PRODUCING MALEIC ANHYDRIDE

[75] Inventors: Youjirou Takahashi; Junichi Toyoda; Toshimasa Kushihara; Ikuo Kurimoto; Shigemi Osaka; Yoshiyuki Nakanishi, all of Himeji, Japan

[73] Assignee: Nippon Shokubai Kagaku Kogyo Co., Ltd., Osaka, Japan

[21] Appl. No.: 842,934

[22] Filed: Mar. 24, 1986

[30] Foreign Application Priority Data

Mar. 26, 1985 [JP] Japan .................................. 60-59627
Feb. 27, 1986 [JP] Japan .................................. 61-40260

[51] Int. Cl.$^4$ ............................................ C07D 307/60
[52] U.S. Cl. ................................................ 549/257
[58] Field of Search ...................................... 549/257

[56] References Cited

U.S. PATENT DOCUMENTS

| | | | |
|---|---|---|---|
| 2,294,130 | 8/1942 | Porter | 549/257 |
| 4,036,780 | 7/1977 | Suzuki et al. | 252/437 |
| 4,097,501 | 6/1978 | Dolhyj et al. | 260/346.74 |
| 4,116,983 | 9/1978 | Schmidt | 260/346.75 |
| 4,118,402 | 10/1978 | Suzuki et al. | 549/257 |
| 4,342,699 | 8/1982 | Palmer et al. | 549/259 |
| 4,564,607 | 1/1986 | Yoneda et al. | 502/409 |

FOREIGN PATENT DOCUMENTS 1130170 10/1968 United Kingdom .

*Primary Examiner*—Mary Lee
*Assistant Examiner*—Bernard I. Dentz
*Attorney, Agent, or Firm*—Sherman and Shalloway

[57] ABSTRACT

An improved process for producing maleic anhydride which comprises catalytically oxidizing benzene with a molecular oxygen-containing gas in the vapor phase in a multitubular heat-exchanger-type reactor. The process is characterized in that a catalyst-packed layer of the reactor is divided into a gas inlet side layer and a gas outlet side layer, the activity of the gas inlet side layer is controlled by adding at least one component selected from the group consisting of potassium, cesium, thallium and rubidium as a promoter or by decreasing the amount of phosphorus pentoxide ($P_2O_5$) to be added in the catalytically active substance containing vanadium pentoxide, molybdenum trioxide and sodium oxide, and the activity of the gas outlet side layer is increased by decreasing the amount of at least one component selected from the group consisting of potassium, cesium, thallium, rubidium, magnesium, calcium, strontium and barium or by not adding such a component from that in the catalyst, or by increasing the amount of phosphorus pentoxide ($P_2O_5$) from the gas inlet side catalyst.

16 Claims, No Drawings

PROCESS FOR PRODUCING MALEIC ANHYDRIDE

This invention relates to a process for producing maleic anhydride which comprises catalytically oxidizing benzene with air or a molecular oxygen-containing gas in the vapor phase in a fixed bed. More specifically, this invention relates to a process for producing maleic anhydride in high yields stably under increased benzene load conditions, and a catalyst therefor.

In order to produce maleic anhydride industrially advantageously by the catalytic vapor phase oxidation of benzene, the catalyst has been required, above all, to have high selectivity and long-term durability. In recent years, there has been a need for energy saving of the process and increased production efficiency, and the catalyst has additionally been required to have the ability to catalyze oxidation of a large amount of benzene with a lesser amount of air, or in other words to have excellent selectivity and durability even when the process is operated in an increased concentration of benzene in a feed gas.

Catalysts heretofore proposed for this purpose cannot fully meet this additional requirement. For example, U.S. Pat. Nos. 4,036,780 and 4,118,402 describe that maleic anhydride is obtained in a yield of as good as 95 to 100% by weight. A review of working examples in these patents, however, shows that such a high yield is obtained only when the concentration of benzene in the feed gas is relatively low, i.e. 40 g/NM$^3$-air (g/NM$^3$ for short). The present inventors have repeated such an example, and found that under oxidation conditions involving an increased benzene concentration of about 50 g/NM$^3$, the temperature of hot spots of the catalyst layer exceeded 500° C., and maleic anhydride was obtained only in a yield of 85 to 90%. Furthermore, in a reaction in which the benzene concentration was as high as more than 50 g/NM$^3$, unusual excessive oxidation, which could not be controlled, occurred in the vicinity of the hot spots of the catalyst layer, and the catalyst was half melted and deactivated. It was further found that with an increasing amount of benzene loaded, the catalytically active substance came off from the surface of the carrier to a greater degree during long-term operation. These facts indicate that it is impossible to apply such catalysts to the high-concentration process.

It is an object of this invention to provide a process for producing maleic anhydride by the catalytic vapor-phase oxidation of benzene with air or a molecular oxygen-containing gas in a fixed bed, which can be operated at a high benzene/air or molecular oxygen-containing gas ratio.

Another object of this invention is to provide a process for producing maleic anhydride which brings about the following advantages.

(1) The energy required for feeding air or a molecular oxygen-containing gas is reduced by decreasing the amount of such a gas to be fed per unit output.

(2) As a result of decreasing the amount of the gas fed per unit output, the amount of heat carried by the gas from the oxidation reactor is decreased and therefore, the amount of heat recovered in the reactor is increased. Consequently, the amount of the very useful high-pressure steam is increased.

(3) By increasing the concentration of maleic anhydride in the product gas, the ratio of maleic anhydride collected by a collector is increased. Thus, the amount of maleic acid collected by a scrubber provided in the rear of the reactor is decreased. Consequently, the energy required for converting maleic acid to maleic anhydride is reduced and the amount of water discharged from the scrubber is decreased.

(4) The production efficiency is increased, and the sizes of the oxidation reactor and accessories per unit output are reduced.

The present inventors have found that with a catalyst prepared by depositing an active substance, which is obtained by adding a particular promoter to vanadium pentoxide ($V_2O_5$), molybdenum trioxide ($MoO_3$) and sodium oxide ($Na_2O$) as basic ingredients, on a porous inorganic inert carrier composed mainly of silicon carbide (SiC) optionally together with a suitable amount of inorganic whiskers, the exfoliation of the catalytically active substance from the carrier surface by mechanical and thermal loads can be greatly reduced.

The present inventors have also found that the loadability of benzene per unit amount of catalyst and catalyst durability can be greatly improved by using a stacked catalyst composed of a catalyst (a first-stage catalyst) disposed in the gas inlet side layer of a catalyst-packed layer and of which activity is controlled by adding (1) at least one component selected from the group consisting of potassium, cesium, thallium and rubidium as a promoter or by (2) decreasing the amount of phosphorus pentoxide ($P_2O_5$) to be added, and a catalyst (a second-stage catalyst) disposed in the gas outlet side layer of the catalyst-packed layer and of which activity is increased by (3) increasing the amount of phosphorus pentoxide ($P_2O_5$) from the first-stage catalyst or (4) by adding at least one component selected from the group consisting of magnesium, calcium, strontium and barium.

Thus, according to this invention, there is provided a process for producing maleic anhydride which comprises catalytically oxidizing benzene with air or a molecular oxygen-containing gas in the vapor phase in a multitubular heat-exchanger-type reactor; wherein a catalyst-packed layer of the reactor is divided into a gas inlet side layer having a height 30 to 70% of the total height of the catalyst packed layer and a gas outlet side layer having a height 70 to 30% of said total height, the gas inlet side layer comprises a catalyst [A] which is either

[A-1] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide ($Na_2O$), 0.01 to 0.05 mole of phosphorus pentoxide ($P_2O_5$) and 0.0001 to 0.5 mole of an oxide of at least one metal selected from the group consisting of potassium, cesium, thallium and rubidium, together with 1 to 20% by weight, based on the active substance, of whiskers having an average diameter of not more than 5 microns and an aspect ratio of from 10 to 500, on a porous inert carrier comprising at least 50% by weight of silicon carbide (SiC) and not more than 10% by weight of aluminum oxide ($Al_2O_3$), or

[A-2] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide (Na$_2$O) and 0 to 0.01 mole of phosphorus pentoxide (P$_2$O$_5$), together with the whiskers defined above, on the carrier defined above, and the gas outlet side layer comprises a catalyst [B] which is either

[B-1] a catalyst prepared by depositing active substance having the same composition as the active substance in catalyst [A-1] except that the content of phosphorus pentoxide is (P$_2$O$_5$) is 0.05 to 0.4 mole, together with the whiskers defined above, on the carrier defined above, or

[B-2] a catalyst prepared by depositing an active substance having the same composition as the active substance in catalyst [A-1] except that the content of phosphorus pentoxide (P$_2$O$_5$) is 0.01 to 0.4 mole and it additionally contains 0.0001 to 0.5 mole of an oxide of at least one metal selected from the group consisting of magnesium, calcium, strontium and barium, together with the whiskers defined above, on the carrier defined above, or

[B-3] a catalyst prepared by depositing an active substance having the same composition as the active substance in catalyst [A-2] except that the content of phosphorus pentoxide ) (P$_2$O$_5$) is 0.01 to 0.2 mole, together with the whiskers defined above, on the carrier defined above.

The active substance of the catalyst provided by this invention is a composition consisting basically of 1 mole of vanadium pentoxide (V$_2$O$_5$) as a main ingredient, 0.3 to 1.0 mole of molydenum trioxide (MoO$_3$), 0.03 to 0.2 mole of sodium oxide (Na$_2$O), 0 to 0.4 mole of phosphorus pentoxide (P$_2$O$_5$), and 0 to 0.5 mole of an oxide of at least one metal selected from the group consisting of potassium cesium, thallium, rubidium, magnesium, calcium, strontium and barium, and the proportions of phosphorus pentoxide, potassium, cesium, thallium, rubidium, magnesium, calcium, strontium and/or rubidium are changed according to the first-stage catalyst and the second-stage catalyst as stated above.

The carrier used is a highly thermally conductive porous inorganic compound comprising at least 50%-by weight, preferably at least 80% by weight, of silicon carbide (SiC), and not more than 10% by weight, preferably not more than 3% by weight, of aluminum oxide (Al$_2$O$_3$) and preferably having an apparent porosity of 10 to 70%, particularly 15 to 40%, and a specific surface area of not more than 1 m$_2$/g. The shape of the carrier is not particularly limited. For example, it may be in the form of a sphere, ring, saddle, solid cylinder or cone having a size of about 3 to 15 mm.

Metallic whiskers and refractory whiskers may be used as the whiskers for use in depositing the catalytically active substance well on the carrier. Examples include metallic whiskers such as tungsten, iron and nickel whiskers, and refractory whiskers such as silicon carbide, silicon nitride, aluminum oxide, titanium carbide, and calcium phosphate whiskers. The whiskers usually have an average diameter of not more than 5 microns, preferably not more than 1 micron, a length of not more than 1,000 microns, preferably not more than 500 microns, and an aspect ratio of from 10 to 500, particularly from 20 to 300.

Deposition of the active substance on the carrier is performed in a conventional manner, for example by preheating the carrier to a temperature of 150° to 250° C., and spraying a solution containing compounds which are sources of active substance onto the surface of the carrier, or by impregnating the carrier in the solution and concentrating the solution. Preferably, the aforesaid whiskers are dispersed in the solution in an amount of 1 to 20% by weight, preferably 3 to 10% by weight, based on the weight of the active substance finally formed. The active substance is deposited in a proportion of 3 to 40 g, preferably 5 to 25 g, per 100 cc of the apparent volume of the carrier.

The reaction in accordance with this invention is carried out after the catalyst is packed into a tube having an inside diameter of 15 to 40 mm, particularly 20 to 30 mm. The first-stage catalyst is disposed in a first portion having a height 30 to 70% of the total height of the catalyst layer in the direction of gas flow, and the second-stage catalyst, in a subsequent portion having a height 70 to 30% of the total height of the catalyst layer.

The first-stage catalyst [A] is [A-1] a catalyst prepared by depositing an active substance composed of 1 mole of vanadium pentoxide (V$_2$O$_5$), 0.3 to 1.0 mole of molybdenum trioxide (MoO$_3$), 0.03 to 0.2 mole of sodium oxide (Na$_2$O), 0.01 to 0.05 mole of phosphorus pentoxide (P$_2$O$_5$) and 0.0001 to 0.5 mole of an oxide of at least one metal selected from the group consisting of potassisum cesium, thallium and rubidium, preferably together with 1 to 20% by weight of the aforesaid whiskers, on the aforesaid porous inert carrier, or [A-2] a catalyst prepared by depositing an active substance composed of 1 mole of vanadium pentoxide (V$_2$O$_5$), 0.3 to 1.0 mole of molybdenum trioxide (MoO$_3$), 0.03 to 0.2 mole of sodium oxide (Na$_2$O) and 0 to 0.01 mole of phosphorus pentoxide (P$_2$O$_5$), preferably together with 1 to 20% by weight of the whiskers defined above, on the carrier defined above.

The second-stage catalyst [B] is [B-1] a catalyst prepared by depositing active substance having the same composition as the active substance in catalyst [A-1] except that the content of phosphorus pentoxide (P$_2$O$_5$) is 0.05 to 0.4 mole. preferably together with 1 to 20% of the whiskers, on the porous carrier, or [B-2] a catalyst prepared by depositing an active substance having the same composition as the active substance in catalyst [A-1] except that the content of phosphorus pentoxide (P$_2$O$_5$) is 0.01 to 0.4 mole and it additionally contains 0.0001 to 0.5 mole of an oxide of at least one metal selected from the group consisting of magnesium, calcium, strontium and barium, preferably together with the aforesaid whiskers, on the porous carrier, or [B-3] a catalyst prepared by depositing an active substance having the same composition as the active substance in catalyst [A-2] except that the content of phosphorus pentoxide (P$_2$O$_5$) is 0.01 to 0.2 mole, preferably together with 1 to 20% by weight of the whiskers, on the porous carrier.

Both the first-stage and second-stage catalysts are converted to finished catalysts by calcining them at a temperature of 350° to 600° C., particularly 400° to 500° C., for 2 to 10 hours under a stream of air or an inert gas.

The catalysts so prepared are used as follows. For example, in a reaction tube immersed in a molten salt bath, the second-stage catalyst is first packed to a height 30 to 70% of the total height of the catalyst layer, and the first-stage catalyst is then stacked over it to a height 70 to 30% of the total height of the catalyst layer. A starting gas composed of a mixture of air or a molecular oxygen-containing gas and 20 to 100 g/NM$^3$, particularly 50 to 80 g/NM$^3$, of benzene and preheated to 100° to 150° C. is passed from the top of the tube through the catalyst layer at a space velocity of 1500 to 6000 hr$^{-1}$, particularly 2000 to 4000 hr$^{-1}$, whereby benzene is oxidized.

Under these high loading conditions, maleic anhydride is obtained in a yield of 95 to 100% by weight (based on 100% pure benzene) stably over an extended period of time. During a long-term operation, variations in reaction temperature are small, and hardly any rise in pressure in the catalyst layer is observed with time. This fact shows that the active substance is not exfoliated from the carrier in spite of the high loading of benzene.

The following examples illustrate the present invention more specifically.

EXAMPLE 1

Oxalic acid (260 g) was dissolved in 1500 cc of water, and 234 g of ammonium metavanadate, 123.6 g of ammonium molybdate, 6.36 g of sodium carbonate, 4.6 g of sodium dihydrogen phosphate and 72.4 g of cesium sulfate were added and dissolved under heat. Furthermore, 21 g of silicon nitride whiskers having an average diameter of 0.5 micron and an average length of 180 microns were added. The mixture was stirred for 30 minutes by an emulsifying machine to prepare a uniformly dispersed slurry.

A porous carrier (1800 cc) in ring form composed of 92% by weight of silicon carbide, 2% by weight of alumina and 6% by weight of silica and having an outside diameter of 7 mm, an inside diameter of 3.5 mm and a length of 7 mm, an apparent porosity of 30% and a specific surface area of 0.04 m$^2$/g was put in a rotary drum equipped with an external heating device. The above slurry was sprayed on the carrier while maintaining it at a temperature of 200° to 250° C. to deposit the active substance on the carrier in an amount of 15 g per 100 cc of the carrier. The carrier thus dried after spraying was then calcined at 400° C. for 5 hours in air to obtain a catalyst IA. This catalyst had an active substance composition (in molar ratio) of $V_2O_5:MoO_3:Na_2O:P_2O_5:Cs_2O=1:0.7:0.06:0.02:0.2$, and the content of the whiskers was 6% by weight based on the active substance.

A catalyst IB having an active substance composition (in molar ratio) of $V_2O_5:MoO_3:Na_2O:P_2O_5:Cs_2O=1:0.7:0.06:0.35:,0.2$ was prepared in the same way as above except that the amount of ammonium dihydrogen phosphate was changed to 80.5 g. The content of the whiskers was 6% by weight based on the active substance.

In a tube having an inside diameter of 25 mm and a length of 3.5 m and immersed in a molten salt bath, catalyst IB was packed to a height of 1.5 m, and the catalyst IA was stacked on it to a height of 1 m, and the temperature in the reaction tube was maintained at 355° C. A gaseous mixture of benzene and air with a benzene concentration of 65 g/NM$^3$ was passed through the tube from its top at a space velocity of 3000 hr$^{-1}$ (STP). Maleic anhydride was obtained in a yield of 98.5% by weight based on 100% pure benzene.

EXAMPLE 2

12N hydrochloric acid (300 cc) was dissolved in 1200 cc of water, and 160 g of ammonium metavanadate, 96.6 g of ammonium molybdate, 8.7 g of sodium carbonate and 6.78 g of ammonium dihydrogen phosphate were dissolved in the solution, and furthermore, 10.5 g of silicon carbide whiskers having an average diameter of 0.2 micron and an average length of 20 microns were added. The mixture was stirred for 30 minutes to form a slurry.

Then, 2000 cc of a porous spherical carrier composed of 88% by weight of SiC, 4% by weight of Al$_2$O$_3$ and 8% by weight of SiO$_2$ and having an average diameter of 6 mm, an apparent porosity of 35% and a specific surface area of 0.03 m$^2$/g was immersed in the slurry prepared as above. The slurry was heated externally to deposit the active substance on the carrier. The amount of the active substance deposited was 8 g per 100 cc of the carrier. The carrier thus treated was then calcined at 430° C. for 6 hours under a stream of air to form a catalyst IIA. This catalyst had an active substance composition (in molar ratio) of $V_2O_5:MoO_3:Na_2O:P_2O_5:=1:0.8:0.12:0.005$ and a whisker content of 5% by weight based on the active substance.

A catalyst IIB having an active substance composition (in molar ratio) of $V_2O_5:MoO_3:Na_2O:P_2O_5=1:0.8:0.12:0.15$ and a whisker content of 5% by weight based on the active substance was prepared in the same way as above except that the amount of ammonium dihydrogen phosphate was changed to 23.4 g.

In a tube having an inside diameter of 25 mm and a length of 3.5 m and immersed in a molten salt bath, catalyst IIB was packed to a height of 1.5 m, and the catalyst IIA was stacked on it to a height of 0.8 m, and the temperature in the reaction tube was maintained at 350° C. A gaseous mixture of benzene and air with a benzene concentration of 60 g/NM$^3$ pre-heated to 120° C. was passed through the tube from its top at a space velocity of 3500 hr$^{-1}$ (STP). Maleic anhydride was obtained in a yield of 96.5% by weight based on 100% pure benzene.

EXAMPLE 3

Oxalic acid (260 g) was dissolved in 1500 cc of water, and 234 g of ammonium metavanadate, 70.6 g of ammonium molybdate, 8.48 g of sodium carbonate, 9.2 g of ammonium dihydrogen phosphate, 20.2 g of potassium nitrate and 44.3 g of rubidium nitrate were dissolved in the solution. Then, 20 g of tungsten whiskers having an average diameter of 0.3 micron and an average length of 80 microns were added and dispersed by a stirrer to form a slurry.

By using the resulting slurry, the active substance was deposited in an amount of 12 g/100 cc of carrier in the same way as in Example 1 on a porous carrier (in pellet form) composed of 90% by weight of SiC, 3% by weight of MgO and 7% by weight of SiO$_2$ and having an apparent porosity of 28%, a specific surface area of 0.05 m$^2$/g, a diameter of 5 mm and a length of 5 mm. The carrier thus treated was then calcined at 450° C. for 4 hours under a stream of air to prepare a catalyst IIIA. The catalyst had an active substance composition (in molar ratio) of $V_2O_5:MoO_3:Na_2O:P_2O_5:K_2O:Rb_2O=1:0.4:0.08:0.04:0.1:0.15$ and a whisker content of 7% by weight based on the active substance.

On the other hand, a catalyst IIIB having an active substance composition (in molar ratio) of $V_2O_5:MoO_3:Na_2O:P_2O_5=1:0.4:0.08:0.18$ and a whisker content of 7% by weight based on the active substance was prepared in the same way as above except that potassium nitrate and rubidium nitrate were not added, and the amount of ammonium dihydrogen phosphate was changed to 41.4 g.

In a tube having an inside diameter of 20 mm and a length of 3.5 m and immersed in a molten salt bath, catalyst IIIB was packed to a height of 1 m, and the catalyst IIIA was stacked on it to a height of 1.8 m, and the temperature in the reaction tube was maintained at 365° C. A gaseous mixture of benzene and a molecular oxygen-containing gas (12% of oxygen, 10% of steam and 78% of nitrogen) with a benzene concentration of 70 g/NM$^3$ pre-heated to 120° C. was passed through the tube from its top at a space velocity of 2800 hr$^{-1}$ (STP). Maleic anhydride was obtained in a yield of 97% by weight based on 100% pure benzene.

EXAMPLE 4

Oxalic acid (260 g) was dissolved in 1500 cc of water, and 234 g of ammonium metavanadate, 106 g of ammonium molybdate, 3.18 g of sodium carbonate and 0.23 g of ammonium dihydrogen phosphate were dissolved in the solution. Furthermore, 11 g of silicon carbide whiskers having an average diameter of 0.4 micron and an average length of 15 microns were added, and the mixture was stirred to form a slurry. By using the resulting slurry, the active substance was deposited on a self-sintered carrier of SiC having a purity of 98.5% (diameter 5.5 mm, spherical) which had an apparent porosity of 25% and a specific surface area of 0.03 m$^2$/g. The carrier having the active substance deposited on it was calcined at 420° C. for 6 hours under a stream of air to obtain a catalyst IVA. The amount of the active substance deposited was 10 g/100 cc of carrier. The resulting catalyst had an active substance composition (in molar ratio) of $V_2O_5:MoO_3:Na_2O:P_2O_5 = 1:0.6:0.03:0.001$, and contained 4% by weight, based on the active substance, of the SiC whiskers.

On the other hand, a catalyst IVB having an active substance composition (in molar ratio) of $V_2O_5:MoO_3:Na_2O:P_2O_5:Tl_2O = 1:0.6:0.03:0.25:0.1$ and contained 4% by weight, based on the active substance, of the whiskers was prepared in the same way as above except that 53.3 g of thalium nitrate was further added, and the amount of ammonium dihydrogen phosphate was changed to 57.5 g.

In a tube having an inside diameter of 25 mm and a length of 3.5 m and immersed in a molten salt bath, catalyst IVB was packed to a height of 1.4 m, and the catalyst IVA was stacked on it to a height of 1.4 m, and the temperature in the reaction tube was maintained at 355° C. A gaseous mixture of benzene and air with a benzene concentration of 60 g/NM$^3$ pre-heated to 120° C. was passed through the tube from its top at a space velocity of 3000 hr$^{-1}$ (STP). Maleic anhydride was obtained in a yield of 99% by weight based on 100% pure benzene.

EXAMPLE 5

Oxalic acid (260 g) was dissolved in 1500 cc of water, and 234 g of ammonium metavanadate, 141 g of ammonium molybdate, 8.5 g of sodium nitrate, 4.6 g of ammonium dihydrogen phosphate, 20.2 g of potassium nitrate and 39 g of cesium nitrate were dissolved in the solution. Then, 11 g of silicon carbide whiskers having an average diameter of 0.3 micron and an average length of 50 microns were added, and the mixture was stirred to form a slurry. By using the resulting slurry, the active substance was deposited on the same carrier as used in Example 1 in the same manner as in Example 1. The carrier thus treated was then calcined in air at 450° C. for 8 hours to form a catalyst VA. The resulting catalyst had an active substance composition (in molar ratio) of $V_2O_5:MoO_3:Na_2O:P_2O_5:Cs_2O:K_2O = 1:0.8:0.05:0.02:0.1:0.1$ and a whisker content of 4% by weight based on the active substance.

A catalyst VB having an active substance composition (in molar ratio) of $V_2O_5:MoO_3:Na_2O:P_2O_5:Cs_2O:BaO = 1:0.8:0.05:0.10:0.1:0.1$ was prepared in the same way as above except that the amount of ammonium dihydrogen phosphate was changed to 23 g, and 26.1 g of barium nitrate was used instead of potassium nitrate.

In a tube having an inside diameter of 25 mm and a length of 3.5 m and immersed in a molten salt bath, catalyst VB was packed to a height of 1.25 m, and the catalyst VA was stacked on it to a height of 1.25 m, and the temperature in the reaction tube was maintained at 355° C. A gaseous mixture of benzene and air with a benzene concentration of 65 g/NM$^3$ was passed through the tube from its top at a space velocity of 3000 hr$^{-1}$ (STP). Maleic anhydride was obtained in a yield of 99.5% by weight based on 100% pure benzene.

COMPARATIVE EXAMPLE 1

Oxalic acid (272 g) was dissolved in 1500 ml of water, and 230 g of ammonium metavanadate, 69.4 g of ammonium molybdate, 11.2 g of trisodium phosphate and 6.7 g of sodium nitrate were successively dissolved. By using this solution, the active substance was deposited on 1800 cc of a self-sintered spherical carrier of SiC with a purity of 98.7% having an apparent porosity of 38%, a specific surface area of 0.05 m$^2$/g and a diameter of 7 to 8 mm. The carrier thus treated was calcined in a stream of air for 8 hours to form a catalyst C. The amount of the active substance deposited was 8 g/100 cc of the carrier, and the catalyst had an active substance composition (in molar ratio) of $V_2O_5:MoO_3:Na_2O:P_2O_5 = 1:0.40:0.06:0.015$.

In a tube having an inside diameter of 25 mm and a length of 3.5 m and immersed in a molten salt bath, catalyst C was packed to a height of 2.5 m, and the temperature in the reaction tube was maintained at 365° C. A gaseous mixture of benzene and air with a benzene concentration of 50 g/NM$^3$ pre-heated to 120° C. was passed through the tube from its top at a space velocity of 3000 hr$^{-1}$ (STP). The temperature of the hot spots reached 5° C., and maleic anhydride was obtained in a yield of only 86% by weight based on 100% pure benzene.

EXAMPLE 6

Catalysts VIA and VIB (the amount of the active substance deposited was 15 g and 12 g/100 cc carrier) were prepared in the same way as in the preparation of catalysts IA and IB in Example 1 except that the whiskers were not used. These catalysts IA+IB and VIA+VIB were used under the same conditions as in Example 1, and the oxidation reaction was carried out for a long period of time. The results are shown in Table 1.

With the catalyst IA+IB, no increase in pressure drop in the catalyst layer was observed with time, and hardly any variations in the yield of maleic anhydride were observed. On the other hand, in the case of the catalyst (VIA+VIB), the amount of the active substance deposited had to be slightly decreased because of the absence of whiskers. Despite this, an increase in pressure drop in the catalyst layer was observed with time. With it, a decrease in the yield of maleic anhydride was observed. This was due to the exfoliation of the active substance from the carrier surface owing to the high loading of benzene. The differences in pressure drop in the initial stage were due to the differences in the extent of exfoliation of the active substances at the time of packing the catalysts into the tube.

TABLE 1

| Catalyst (IA + IB) | | Catalyst (VIA + VIB) | |
|---|---|---|---|
| Yield of maleic anhydride (wt. %) | Pressure drop in the catalyst layer (mm water) | Yield of maleic anhydride (wt. %) | Pressure drop in the catalyst layer (mm water) |
| Initial stage | 98.5 | 3100 | 98.0 | 3350 |
| 1 month later | 98.7 | 3100 | 97.3 | 3430 |
| 2 months later | 98.4 | 3100 | 97.2 | 3540 |
| 3 months later | 98.5 | 3100 | 96.8 | 3610 |

EXAMPLE 7

A catalyst VIIA was prepared in the same way as in the preparation of catalyst IA except that 106.6 g of thalium nitrate was used instead of 72.4 g of cesium sulfate. The same reaction as in Example 1 was carried out using catalysts VIIA and IB. The results are shown in Table 2.

EXAMPLE 8

A catalyst VIIIB was prepared in the same way as in the preparation of catalyst IB except that the amount of ammonium dihydrogen phosphate was changed to 23 g, the amount of cesium sulfate was changed to 54.3, and 27.2 g of calcium sulfate was further added. The same reaction as in Example 1 as carried out using catalysts IA and VIIIB. The results are shown in Table 2.

EXAMPLE 9

A catalyst IXB was prepared in the same way as in the preparation of catalyst IB except that the amount of ammonium dihydrogen phosphate was changed to 23 g, 17.4 g of potassium sulfate was used instead of cesium sulfate, and 18.1 g of magnesium sulfate and 6.3 g of strontium nitrate were further added. The same reaction as in Example 1 was carried out using catalysts IA and IXB.

EXAMPLE 10

A catalyst XA was prepared in the same way as in the preparation of catalyst IA except that 60.7 g of potassium nitrate was used instead of 72.4 g of cesium sulfate.

A catalyst XB was prepared in the same way as in the preparation of catalyst IB except that the amount of ammonium dihydrogen phosphate was changed to 23 g, 14.8 g of rubidium nitrate was used instead of cesium sulfate, and 23.3 g of barium sulfate was used additionally.

The same reaction as in Example 1 was carried out using catalysts XA and XB. The results are shown in Table 2.

TABLE 2

| | 1st stage catalyst / 2nd stage catalyst | Composition of the active substance (in molar ratio) | Yield of maleic anhydride (wt. % based on 100% pure benzene) |
|---|---|---|---|
| Example 7 | VIIA | $V_2O_5:MoO_3:Na_2O:P_2O_5:Tl_2O = 1:0.7:0.06:0.02:0.2$ | 97.5 |
| | IB | $V_2O_5:MoO_3:Na_2O:P_2O_5:Cs_2O = 1:0.7:0.06:0.35:0.2$ | |
| Example 8 | IA | $V_2O_5:MoO_3:Na_2O:P_2O_5:Cs_2O = 1:0.7:0.06:0.02:0.2$ | 99.1 |
| | VIIIB | $V_2O_5:MoO_3:Na_2O:P_2O_5:Cs_2O:CaO = 1:0.7:0.06:0.1:0.15:0.2$ | |
| Example 9 | IA | $V_2O_5:MoO_3:Na_2O:P_2O_5:Cs_2O = 1:0.7:0.06:0.02:0.2$ | 98.5 |
| | IXB | $V_2O_5:MoO_3:Na_2O:P_2O_5:K_2O:MgO:SrO = 1:0.7:0.06:0.1:0.1:0.15:0.03$ | |
| Example 10 | XA | $V_2O_5:MoO_3:Na_2O:P_2O_5:K_2O = 1:0.7:0.06:0.02:0.3$ | 99.0 |
| | XB | $V_2O_5:MoO_3:Na_2O:P_2O_5:Rb_2O:BaO = 1:0.7:0.06:0.1:0.05:0.1$ | |

What is claimed is:

1. A process for producing maleic anhydride which comprises catalytically oxidizing benzene at a concentration of 50 to 100 g/NM$^3$ with air or a molecular oxygen-containing gas in the vapor phase in a multitubular heat-exchanger-type reactor; wherein a catalyst-packed layer of the reactor is divided into a gas inlet side layer having a height 30 to 70% of the total height of the catalyst packed layer and a gas outlet side layer having a height 70 to 30% of said total height, the gas inlet side layer comprises a catalyst [A] which is either

[A-1] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide ($Na_2O$), 0.01 to 0.05 mole of phosphorus pentoxide ($P_2O_5$) and 0.0001 to 0.5 mole of an oxide of at least one metal selected from the group consisting of potassium, cesium, thallium and rubidium on a porous inert carrier comprising at least 50% by weight of silicon carbide (SiC) and not more than 10% by weight of aluminum oxide ($Al_2O_3$), or

[A-2] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide ($Na_2O$) and 0 to 0.01 mole of phosphorus pentoxide ($P_2O_5$) on the carrier defined above, and the gas outlet side layer comprises a catalyst [B] which is either

[B-1] a catalyst prepared by depositing active substance having the same composition as the active substance in catalyst [A-1] except that the content of phosphorus pentoxide ($P_2O_5$) is 0.05 to 0.4 mole on the carrier defined above, or

[B-2] a catalyst prepared by depositing an active substance having the same composition as the active substance in catalyst [A-1] except that the content of phosphorus pentoxide ($P_2O_5$) is 0.01 to 0.4 mole and it additionally contains 0.0001 to 0.5 mole of an oxide of at least one metal selected from the group consisting of magnesium, calcium, strontium and barium on the carrier defined above, or

[B-3] a catalyst prepared by depositing an active substance having the same composition as the active substance in catalyst [A-2] except that the content of phosphorus pentoxide is ($P_2O_5$) is 0.01 to 0.2 mole on the carrier defined above.

2. The process of claim 1 wherein the carrier is a porous inert carrier comprising at least 80% of silicon carbide and not more than 3% by weight of aluminum oxide.

3. The process of claim 1 wherein the carrier is a self-sintered porous inert carrier comprising at least 98% by weight of silicon carbide.

4. The process of claim 1 wherein the carrier is in the form of a sphere, ring, solid cylinder, saddle, cone or block.

5. A process for producing maleic anhydride which comprises catalytically oxidizing benzene at a concentration of 50 to 100 g/$NM^3$ with air or a molecular oxygen-containing gas in the vapor phase in a multitubular heat-exchanger-type reactor; wherein a catalyst-packed layer of the reactor is divided into a gas inlet side layer having a height 30 to 70% of the total height of the catalyst packed layer and a gas outlet side layer having a height 70 to 30% of said total height, the gas inlet side layer comprises a catalyst [A] which is either

[A-1] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide ($Na_2O$), 0.01 to 0.05 mole of phosphorus pentoxide ($P_2O_5$) and 0.0001 to 0.5 mole of an oxide of at least one metal selected from the group consisting of potassium, cesium, thallium and rubidium, together with 1 to 20% by weight, based on the active substance, of whiskers having an average diameter of not more than 5 microns and an aspect ratio of from 10 to 500, on a porous inert carrier comprising at least 50% by weight of silicon carbide (SiC) and not more than 10% by weight of aluminum oxide ($Al_2O_3$), or

[A-2] a catalyst prepared by depositing an active substance composed of 1 mole of vanadium pentoxide ($V_2O_5$), 0.3 to 1.0 mole of molybdenum trioxide ($MoO_3$), 0.03 to 0.2 mole of sodium oxide ($Na_2O$) and 0 to 0.01 mole of phosphorus pentoxide ($P_2O_5$), together with the whiskers defined above, on the carrier defined above, and the gas outlet side layer comprises a catalyst [B] which is either

[B-1] a catalyst prepared by depositing active substance having the same composition as the active substance in catalyst [A-1] except that the content of phosphorus pentoxide ($P_2O_5$) is 0.05 to 0.4 mole, together with the whiskers defined above, on the carrier defined above, or

[B-2] a catalyst prepared by depositing an active substance having the same composition as the active substance in catalyst [A-1] except that the content of phosphorus pentoxide ($P_2O_5$) is 0.01 to 0.4 mole and it additionally contains 0.0001 to 0.5 mole of an oxide of at least one metal selected from the group consisting of magnesium, calcium, strontium and barium, together with the whiskers defined above, on the carrier defined above, or

[B-3] a catalyst prepared by depositing an active substance having the same composition as the active substance in catalyst [A-2] except that the content of phosphorus pentoxide ($P_2O_5$) is 0.01 to 0.2 mole, together with the whiskers defined above, on the carrier defined above.

6. The proces of claim 5 wherein the carrier is a porous inert carrier comprising at least 80% of silicon carbide and not more than 3% by weight of aluminum oxide.

7. The process of claim 5 wherein the carrier is a self-sintered porous inert carrier comprising at least 98% by weight of silicon carbide.

8. The process of claim 5 wherein the carrier is in the form of a sphere, ring, solid cylinder, saddle, cone or block.

9. The process of claim 1 wherein the catalyst-packed layer comprises the catalyst A-1 on the gas inlet side layer and the catalyst B-1 on the gas outlet side layer.

10. The process of claim 1 wherein the catalyst-packed layer comprises the catalyst A-1 on the gas inlet side layer and the catalyst B-2 on the gas outlet side layer.

11. The process of claim 1 wherein the catalyst-packed layer comprises the catalyst A-2 on the gas inlet side layer and the catalyst B-3 on the gas outlet side layer.

12. The process of claim 5 wherein the catalyst-packed layer comprises the catalyst A-1 on the gas inlet side layer and the catalyst B-1 on the gas outlet side layer.

13. The process of claim 5 wherein the catalyst-packed layer comprises the catalyst A-1 on the gas inlet side layer and the catalyst B-2 on the gas outlet side layer.

14. The process of claim 5 wherein the catalyst-packed layer comprises the catalyst A-2 on the gas inlet side layer and the catalyst B-3 on the gas outlet side layer.

15. The process of claim 5 wherein the concentration of benzene in air is from 50 g to 80 g benzene per $NM^3$-air.

16. The process of claim 1 wherein the concentration of benzene in air is from 50 g to 80 g benzene per $NM^3$-air.

* * * * *